US006755073B2

(12) United States Patent
Jakoby et al.

(10) Patent No.: US 6,755,073 B2
(45) Date of Patent: Jun. 29, 2004

(54) SENSOR FOR MEASURING THE VISCOSITY OF A LIQUID

(75) Inventors: Bernhard Jakoby, Vienna (AT); Matthias Buskies, Eningen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/332,830

(22) PCT Filed: May 8, 2002

(86) PCT No.: PCT/DE02/01661

§ 371 (c)(1), (2), (4) Date: Jun. 16, 2003

(87) PCT Pub. No.: WO02/093136

PCT Pub. Date: Nov. 21, 2002

(65) Prior Publication Data

US 2003/0217589 A1 Nov. 27, 2003

(30) Foreign Application Priority Data

May 11, 2001 (DE) ........................................ 101 23 040

(51) Int. Cl.[7] ................................................ G01N 11/16

(52) U.S. Cl. .................... 73/54.41; 73/54.23; 73/54.24; 73/54.25

(58) Field of Search ............................ 73/54.23, 54.24, 73/54.25, 54.41, 54.01

(56) References Cited

U.S. PATENT DOCUMENTS

| | | | | | |
|---|---|---|---|---|---|
| 4,741,200 | A | * | 5/1988 | Hammerle | 73/54.25 |
| 5,201,215 | A | * | 4/1993 | Granstaff et al. | 73/54.41 |
| 5,324,542 | A | | 6/1994 | Modic | |
| 5,734,098 | A | * | 3/1998 | Kraus et al. | 73/61.62 |
| 6,223,588 | B1 | * | 5/2001 | Burgass et al. | 73/53.01 |
| 6,357,278 | B1 | * | 3/2002 | Sivavec et al. | 73/24.01 |
| 6,432,362 | B1 | * | 8/2002 | Shinar et al. | 422/82.01 |
| 6,500,547 | B1 | * | 12/2002 | Potyrailo | 428/422 |
| 2003/0000291 | A1 | * | 1/2003 | Kolosov et al. | 73/61.52 |
| 2003/0053936 | A1 | * | 3/2003 | Potyralio et al. | 422/82.11 |

FOREIGN PATENT DOCUMENTS

| | | | |
|---|---|---|---|
| DE | 196 44 290 | 5/1998 | |
| DE | 197 34 706 | 2/1999 | |
| DE | 101 12 433 | 10/2002 | 73/54.24 |
| WO | WO 00 33051 | 6/2000 | |

* cited by examiner

*Primary Examiner*—Daniel S. Larkin
(74) *Attorney, Agent, or Firm*—Kenyon & Kenyon

(57) ABSTRACT

A sensor for measuring the viscosity of a fluid, which has an oscillator. The oscillator is dipped into the fluid. The surface of the oscillator is provided with a dirt-repellent coating.

8 Claims, 1 Drawing Sheet

2
1
21
22
32
31
3

SENSOR FOR MEASURING THE VISCOSITY OF A LIQUID

BACKGROUND INFORMATION

Sensors for measuring the viscosity of a fluid are already known from German Patent Application No. 101 12 433.3. When working with sensors of this type, an oscillator is inserted into a fluid, and the oscillation frequency and the damping of the oscillation are observed. The viscosity of the surrounding fluid may be inferred based on a shift of the oscillation frequency and/or an altered damping.

SUMMARY OF THE INVENTION

The sensor of the present invention for measuring the viscosity of a fluid has the advantage that the accumulation of dirt on the surface of the oscillator is prevented or markedly reduced by a dirt-repellent coating. The long-term durability of the sensors is thus improved.

Modified, oligomeric polysiloxane coatings or fluorine-containing plastic coatings are considered in particular as dirt-repellent coatings. In this context, the layer thickness is perceptibly less than the penetration of an undulation into the fluid, i.e. less than 1 $\mu$m, particularly less than 0.5 $\mu$m. The oscillator preferably takes the form of a shear-mode transducer, since this oscillation mode exhibits a particularly strong dependence on the viscosity. Preferably a quartz plate from a so-called simply (singly) rotated section, as, for example, the AT section is used The oscillator is excited to oscillate particularly simply by applied electrodes which are formed as surface metallizations.

DETAILED DESCRIPTION

Figure 1:
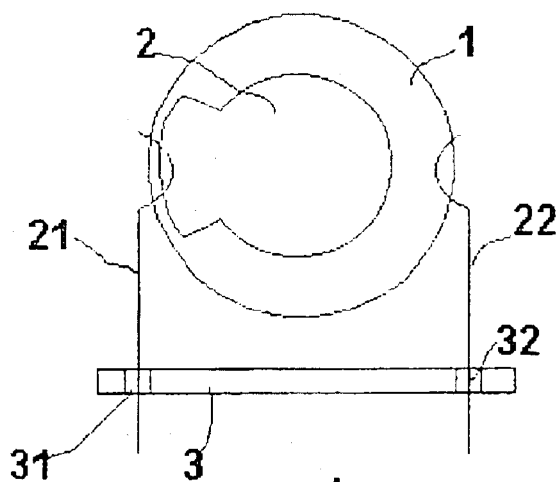
FIG. 1 shows a front view of a sensor.
Figure 2:
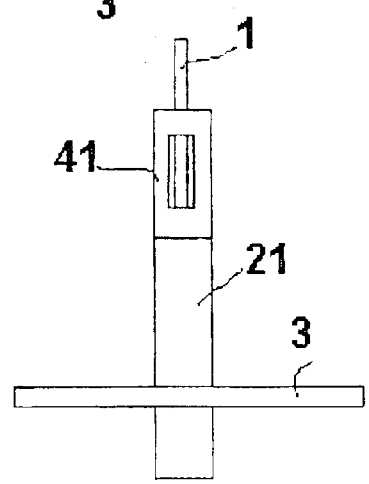
FIG. 2 shows a side view of a sensor.

FIG. 1 shows a front view and FIG. 2 shows a side view of a sensor according to the invention for measuring the viscosity of a fluid. The sensor has an oscillator 1 which is formed in particular as a quartz disk. On the front, as shown in FIG. 1, an electrode 2 is applied which takes the form of a thin, superficial metallization layer. Moreover, a corresponding electrode is formed on the back of oscillator 1, i.e., on the side not visible in FIG. 1. Electrode 2 extends into an edge area in which it is contacted by a conductive spring 21. A second conductive spring 22 is also provided, by which the correspondingly formed electrode on the back of oscillator 1 is contacted. Therefore, the rear view looks just the same as the front view, with the difference that spring 22 contacts the electrode on the back side. The contact between the springs and the electrodes is produced by conductive adhesive, and is not shown in the Figures. Furthermore, conductive springs 21, 22 take over the retaining functions, i.e., oscillator 1 is mechanically supported by these springs. On their part, springs 21, 22 are held by a base plate 3. Base plate 3 may either be made from an electrically insulating material, or else, as shown in FIG. 1, from an electrically conductive material, insulating lead-throughs 31 and 32 then being provided by which springs 21 and 22 are held in an insulating manner. If an insulating material is used as material for support 3, these insulating lead-throughs 31, 32 are naturally superfluous.

FIG. 2 shows a side view of the sensor according to FIG. 1, onto spring 21. As can be seen, spring 21 has an upper receiving area 41, in which spring 21 is bent toward the center point of oscillator 1, and also has an elongated slot. Thus, spring 21 is formed as a leaf spring and may be processed particularly easily by punching and bending. In this way, a particularly simple retaining device is created for oscillator 1 which may be produced very easily from the standpoint of production engineering.

The sensor is dipped into fluid whose viscosity is to be measured. Oscillator 1 is excited to oscillate mechanically by applying electrical voltages to electrodes 2 on the front and back of oscillator 1. Considered here as material for oscillator 1 is, in particular, simply rotated quartz sections in which so-called shear vibrations are produced by applying electrical fields. Due to electrodes 2 on the front and back of the oscillator, an electrical field is generated between these two electrodes which is perpendicular to the surface of oscillator 1. When working with simply rotated quartz sections, the behavior is such that due to the electrical field, oscillations are generated in the quartz which are oriented perpendicular to the electrical field.

Figure 3:
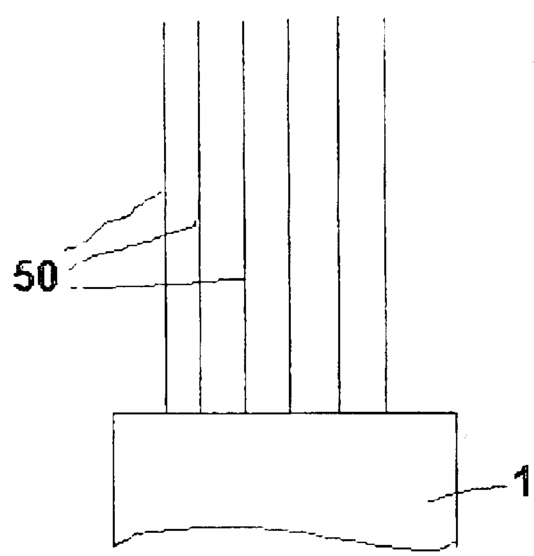
FIGS. 3 and 4 illustrate the functioning of a sensor.
Figure 4:
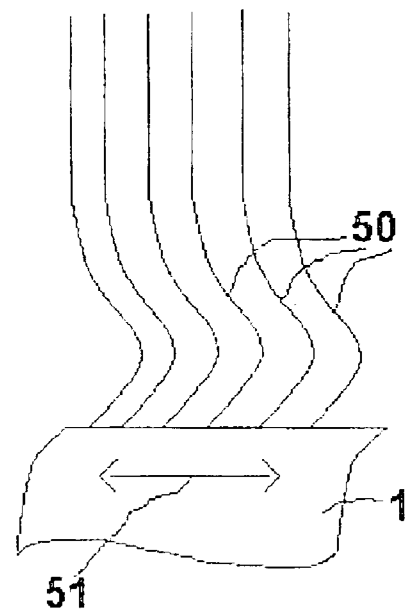

Shear vibrations are clarified in FIGS. 3 and 4. A quartz oscillator 1 is shown schematically in FIG. 3 without the application of an electrical field. Marks 50 which are perpendicular to the surface of oscillator 1 indicate a fluid which is calm in FIG. 3, since oscillator 1 is not oscillating. FIG. 4 now shows the excited state, i.e. oscillator 1 is oscillating here parallel to its surface, as shown clearly by arrow 51. The effect on the fluid is shown by lines 50 which are now bent. In the immediate vicinity with respect to the surface of oscillator 1, the fluid is carried along, that is to say, the fluid follows the movement of oscillator 1. Therefore, a movement of the fluid is caused which is likewise parallel to the surface of oscillator 1. This form of oscillation naturally also continues in the fluid accordingly, so that even at a small distance to the surface of oscillator 1, movements of the fluid take place. In an area lying further from the surface of oscillator 1, the fluid is then calm again, as is shown clearly by lines 50 which are then running straight again. Typically, the vibrations caused by the shear vibration are only able to penetrate a few $\mu$m, or even in the sub-micron range, into a fluid. The oscillation properties of oscillator 1 are influenced by the carrying along of the fluid in the region near the surface of oscillator 1. In particular, the oscillation frequency of oscillator 1 and the damping of oscillator 1 are influenced. This influence is dependent on the viscosity and the density of the fluid. Since particularly for applications in media sensors, the density of fluids fluctuates only slightly, the effect of the fluid on the oscillation of oscillator 1 is therefore determined essentially by the viscosity. Since the undulation penetrates only a few $\mu$m into the fluid, the effect on oscillator 1 is determined essentially by the superficial fluid layer. When dirt deposits on the surface of oscillator 1, the oscillation of oscillator 1 is strongly influenced by it. In particular, it may then occur that the oscillation of oscillator 1 is determined essentially by this deposited layer, and no longer by the viscosity of the fluid.

According to the invention, it has now turned out that dirt-repellent surface coatings are also suitable for such viscosity sensors. By a suitable surface coating which prevents dirt from depositing on the surface of oscillator 1, it is possible to prevent the deposit of dirt on the surface without thereby influencing the measurement of the viscosity. It may be that the measuring principle is based on adhesion of the fluid to the surface, so that a coating which hinders adhesion to the surface should really be detrimental to the measuring principle. However, it has turned out that a number of dirt-repellent surface coatings may be used without impairing the measuring function of the sensor. Moreover, the oscillation should not be hindered by the surface coating. In this context, thick, organic coatings in particular, which, for example, could lead to a viscoelastic damping of the oscillation, may be problematic. Such coatings would then even cause so strong a damping that a reasonable measurement of the viscosity would be hindered. According to the present invention, it has now emerged that dirt-repellent surface coatings may be applied without at the same time substantially impairing the oscillation of oscillator 1 and thus also the measurement of the viscosity.

Modified oligomeric polysiloxanes have proven to be worthwhile as a possible coating. Such polysiloxanes are familiar as dirt-hindering and graffti-hindering surface coatings. A coating of this type is marketed, for example, under the name Polysiloxane 704 and 705 by the firm Kissler Marketing and Partner, Kleiner Weg 17,97877 Wertheim.

Fluoroplastics which may be applied in thin superficial layers are also suitable as surface coatings. Such thin surface coatings are also known as antispread agents. A surface coating of this type is offered, for example, under the product name Antispread F2/50FK60 by the firm Dr. Tillwich GmbH, Murrbachsteige 26, 72160 Horb.

Generally, all dirt-repellent layers are suitable which can be produced to be sufficiently thin, i.e., in particular thinner than a layer thickness of 1 $\mu$m, especially less than a layer thickness of 0.5 $\mu$m.

The sensor element shown in the Figures having a suitable surface coating is usable in particular as a viscosity sensor for oil in an engine compartment. In this case, due to the superficial coating, a deposit of dirt particles on oscillator 1 is reduced or at least prevented to the extent that the viscosity of the oil may be measured over a long period of time. The sensor may be used particularly in an engine in a motor vehicle in order to give evidence about the quality of the engine lubricant based on the viscosity. In light of the viscosity of the oil, it is then possible in particular to determine whether it is necessary to change the oil. It may thus be ensured that motor oil of a motor vehicle is always first changed when an oil change is necessary based on the change in viscosity. Thus, the servicing frequency of motor vehicles may be reduced or adjusted to an actual need.

Here, the method was described in terms of a quartz plate which dips relatively freely into the fluid. However, all other micro-acoustic viscosity sensors which emit a vibration, particularly a shear vibration, into the fluid are also suitable. Such elements are also realized, for example, in the form of surface-wave components. Surface-wave components of this kind are often implemented as traversed distances, in which the propagation time of a superficial wave is measured. The propagation time of the wave is influenced by a fluid and is a function, inter alia, of the viscosity of the fluid. The damping of the wave is also influenced by the viscosity. Moreover, piezoelectric materials other than the quartz described here may also be used.

What is claimed is:

1. A sensor for measuring the viscosity of a fluid, comprising:

a piezoelectric oscillator for introducing into the fluid, the oscillator having oscillation properties which are a function of the viscosity of the fluid, the oscillator having a surface having a dirt-repellent coating.

2. The sensor according to claim 1, wherein the coating includes a layer of a modified, oligomeric polysiloxane.

3. The sensor according to claim 1, wherein the coating includes a layer of an antispread agent based on fluoroplastics.

4. The sensor according to claim 1, wherein the coating has a layer thickness of less than 1 $\mu$m.

5. The sensor according to claim 1, wherein the coating has a layer thickness of less than 0.5 $\mu$m.

6. The sensor according to claim 1, wherein the oscillator includes a shear-mode transducer.

7. The sensor according to claim 1, wherein the oscillator is a quartz oscillator on a simply rotated quartz substrate.

8. The sensor according to claim 1, further comprising electrodes situated on the oscillator.

* * * * *